United States Patent [19]
Etingher

[11] Patent Number: 4,776,325
[45] Date of Patent: Oct. 11, 1988

[54] EXTERNAL PENILE SUPPORT DEVICE AND METHOD

[75] Inventor: Constantin Etingher, Canby, Oreg.

[73] Assignee: Companion Medical Products Corporation, La Jolla, Calif.

[21] Appl. No.: 40,786

[22] PCT Filed: Sep. 18, 1986

[86] PCT No.: PCT/US86/01948
§ 371 Date: Sep. 18, 1986
§ 102(e) Date: Sep. 18, 1986

[87] PCT Pub. No.: WO88/01856
PCT Pub. Date: Mar. 24, 1988

[51] Int. Cl.$^4$ .................................................. A61F 5/41
[52] U.S. Cl. ....................................................... 128/79
[58] Field of Search ........................................... 128/79

[56] References Cited
U.S. PATENT DOCUMENTS

| | | |
|---|---|---|
| 2,818,855 | 1/1958 | Miller ..................................... 128/79 |
| 3,920,007 | 11/1975 | Line ....................................... 128/79 |
| 4,362,152 | 12/1982 | Gorokhovsky et al. ............... 128/79 |
| 4,449,521 | 5/1984 | Panzer .................................... 128/79 |

FOREIGN PATENT DOCUMENTS

| | | | |
|---|---|---|---|
| 545721 | 2/1932 | Fed. Rep. of Germany ........ | 128/79 |
| 154637 | 11/1963 | U.S.S.R. ................................ | 128/79 |
| 178044 | 12/1963 | U.S.S.R. ................................ | 128/79 |
| 443667 | 4/1975 | U.S.S.R. ................................ | 128/79 |
| 589978 | 1/1978 | U.S.S.R. ................................ | 128/79 |
| 782809 | 11/1980 | U.S.S.R. ................................ | 128/79 |

Primary Examiner—John J. Wilson
Assistant Examiner—Cary E. Stone
Attorney, Agent, or Firm—David J. Harshman

[57] ABSTRACT

An improved external penile support device for aiding penile erection comprises an elongated rod with first and second ends, a yoke coupled at the first end including arcuate arms adapted for and encircling the glans of the penis, a supporting arc portion at the second end being contoured to conform to the pubic muscles, the rod having an upward bend with respect to the longitudinal axis, and a strap at the second end for securing the device to the penis. It further comprises an element for applying pressure to the dorsal vein at the top of the root of the penis, which has a generally flat base surface portion for contacting the penis for restricting flow of blood. The rod includes a core and filament wrapped thereon.

2 Claims, 7 Drawing Sheets

EXTERNAL PENILE SUPPORT DEVICE AND METHOD

BACKGROUND OF THE INVENTION

1. Field of the Invention

This invention relates to a device used in the treatment of male impotency, and in particular to an external penile support device and method for stimulating and maintaining a penile erection.

2. Description of the Prior Art

Different kinds of devices are available for overcoming the impotency problem. One type of device is penile implants where semi-rigid rods are inserted in the erectile chambers permitting stiffening of the penis position to cause erection. Implantation of these kinds of devices can lead to total inorganic impotence in cases where there may have been only psychogenic or partial organic impotence.

Other types of devices are externally applied support devices of the type which are non-invasive. One device for treating impotency is that described by Gorokhovsky in U.S. Pat. No. 4,362,152 for an erector device. The device comprises a prosthetic erector for for remedying problems of impotency in males by using a pair of substantially rigid rods encased within a common elastic encasement in a side-by-side relation. The rods have a first end having a yoke defined by first and second arms forming a pair of spaced apart, generally hook-shaped arcuate arms which are adapted for encircling the glans of the penis around and in abutment with the penis corona. Securement means are provided at the second end of the rod for securing the erector to the penis. The rods have a bend located at a station about one-third of the length of the rod away from the first end, the bend contacting the penis superficial dorsal vein for applying pressure to the veins. The purpose is to constrict flow of blood that would otherwise leave the penis, thereby causing the penis to become engorged with blood to cause an erection. The second end of each rod also has a bend surrounded by an enlarged encasement for contacting and applying pressure to the penis superficial dorsal vein and corpora cavernosa. The securement means is capable of stretching and retracting in response to corresponding changes in penile erection, and expansion of the glans causes the arms of the yoke to rotate relatively further apart causing the second ends of the rods to rotate relatively closer together. This stretches the securement means and causes the second ends of the rods to exert increasing pressure on the dorsal vein and corpora cavernosa without causing pressure on the arterial vessels and corpus cavernosum urethra.

Another device for treating impotency is that described in Russian Pat. No. 178,044 by Ploticher, et al. It comprises retaining rods within a common case, and has extremities of its yoke abutting at a single point of contact which results in one extremity projecting beyond the other.

Such conventional devices do not have a structure that is necessarily comfortable to the wearer of the device in that each incorporates by its design protruding elements and encasements which may tend to inhibit the effectiveness of the device. For example, the action of the prior art devices in applying pressure to the superficial dorsal vein may be inhibited by a design which does not necessarily engage or apply pressure to the vein but may miss the vein in its operation. In addition, the protruding elements may push into the fleshy part of the penis and yet miss the veins so that the operation of the device is uncomfortable and less than optimum in terms of stimulating and maintaining an erection.

The structure of conventional devices and their manufacture are of such a type that there is a combination of differing materials and assembly of parts such that there may be crevices and portions of the device which could readily provide an environment for bacterial growth and the like. It is imperative in such sensitive areas involving sex organs that the device not have crevices and portions where such bacterial growth could occur, and such growth leading to causes of infection is not healthful in this sensitive area of medical devices.

Another problem with the prior art is that the typical materials used are such that they are or can be corrosive, and there is no traceability and consistency regarding the manufacture and assembly of such devices, since each device under conventional methods must be individually manufactured and measured for individual use in each patient's case. Another problem with conventional support devices of the type mentioned above is that such devices encounter the problem of increased manufacturing costs and lack of durability due to the assembly steps required. Also, the structure of the unit is typically such that it may be prohibitive in the costs of manufacturing same.

Another problem with the prior art devices is that they utilize an assemblage of a number of differing parts which causes problems in the reliability and durability of the unit, in that it can become disassembled and possibly deteriorate during use. This may cause injury to the user therof or to the user's partner during coitus, and could have devastating effects on the treatment of the patient.

Another problem encountered in the prior art devices is that the design and structure utilized may not be conducive and convenient for the user thereof to fit the device onto the penis in a comfortable fashion. Because of the manner of the design, there can be problems encountered in attempting to secure the device to the penis and scrotum area. In many instances, the conventional prior art devices may cause extreme pain if not properly fit and properly adjusted prior to use by the user thereof.

Conventional external penile support devices have the additional problem of not being adapted to readily retain their shape, and to be comprised of parts in standard sizes which can be assembled to fit any user in need of an external device.

Finally, conventional external penile support devices do not provide an easily fitted reliable and durable device which has improved characteristics in terms of aiding and maintaining an erection for the user thereof.

SUMMARY OF THE INVENTION

It is an object of the present invention to construct an improved external penile support device and a method therefor which is simple and efficient to manufacture.

It is another object of the present invention to construct an improved external penile support device having an effective and reliable means for applying pressure to the dorsal vein without causing discomfort to the user of the device.

It is a further object of the present invention to construct an external penile support device which is suited for operating in an environment which does not have areas where matter can collect for bacterial growth to occur.

It is yet another object of the present invention to provide an external support device which efficiently and effectively applies pressure to the superficial dorsal veing so as to stimulate and maintain an erection.

It is yet another object of the present invention to construct an external penile support device which utilizes materials suitably adapted to the medical environment for sterilization, and adapted to traceability and medical fitness for operating in a germ-free environment.

It is another object of the present invention to construct an external penile support device which has less number of parts in operation so as to permit construction thereof at reduced manufacturing costs and increased reliability and durability of each device in repeated operations.

It is yet another object of the present invention to provide an external penile support device which has less likelihood of becoming disassembled and deteriorating during use so as to prevent causing harm to the user thereof.

It is a further object of the present invention to construct an external penile support device which is convenient for the user to use and fit, yet offer improved reliability without causing pain and other problems which would effect the ability to maintain an erection.

It is yet a further object of the present invention to construct an external penile support device which utilizes standardized sizes of parts which when formed together permit repeatability and reliability of sizes so as to permit improved quality control at a reduced cost.

It is yet another object of the present invention to utilize a method for manufacturing same in a cost-effective and efficient manner.

It is a further object of the present invention to provide a method for measuring the penis for determining the parameters necessary to allow manufacture of the item.

It is still a further object of the present invention to present a method of systems and procedures for manufacturing an improved external penile support device.

Further objects of the present invention will become apparent in the full description of the invention taken in conjunction with the drawings set forth below.

An improved external penile support device for aiding penile erection of the type having an elongated rod means having first and second ends, a yoke coupled at the first end including arcuate arms adapted for and encircling the glans of the penis, a supporting arc portion at the second end being contoured to conform to the pubic muscles, the rod means having an upward bend with respect to the longitudinal axis, and securement means at the second end for securing the device to the penis, wherein the improvement comprises: said supporting arc portion further comprising means for applying pressure to the dorsal vein at the top of the root of the penis comprising a generally flat base for restricting flow of blood without discomfort.

DETAILED DESCRIPTION OF THE DRAWINGS

Figure 1:
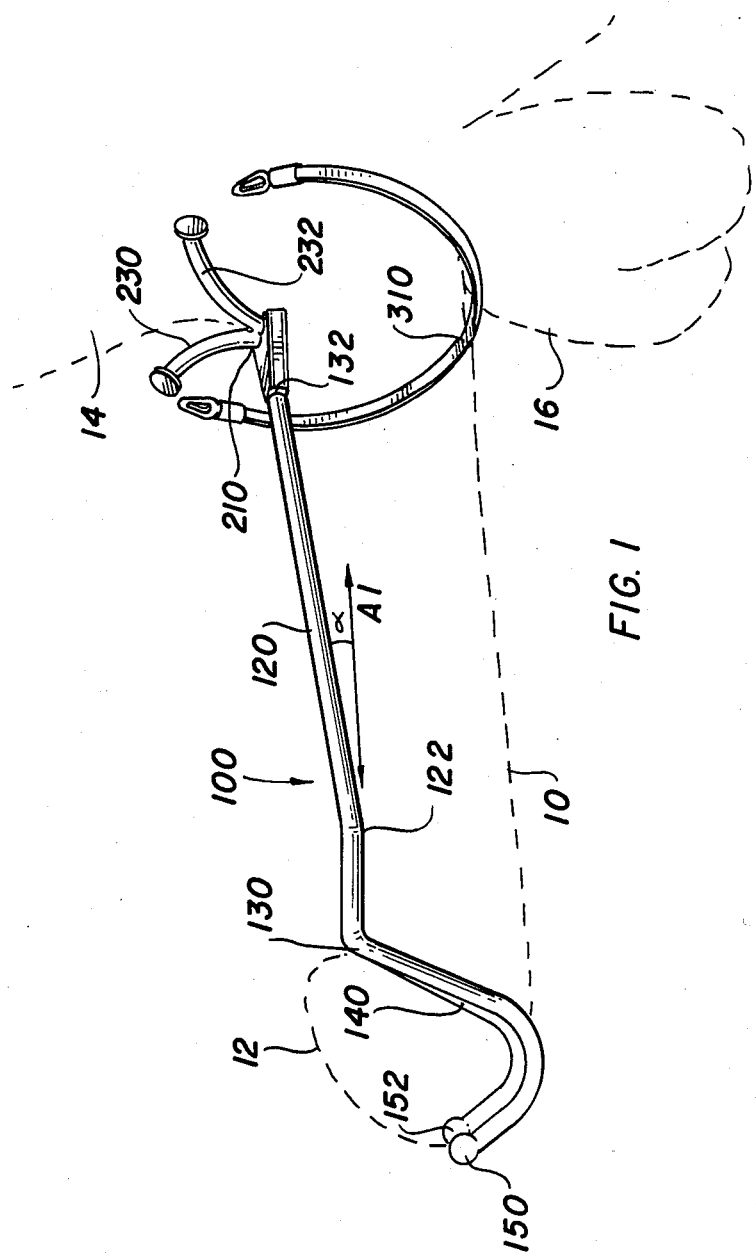
FIG. 1 is a perspective view of a preferred embodiment of an improved external penile support device in accordance with the present invention.

In describing a preferred embodiment of the invention illustrated in the drawings, specific terminology will be resorted to for the sake of clarity. However, the invention is not intended to be limited to the specific terms so selected, and it is to be understood that each specific term includes all technical equivalents which operate in a similar manner to accomplish a similar purpose.

Referring to the drawings, in FIG. 1 there is shown in perspective a preferred embodiment of an external penile support device 100 showing it supporting an erect penis 10. The device 100 comprises an elongated rod means 120 having first and second ends 130, 132 respectively. A yoke means 140 is coupled at the first end 130 and includes a pair of arcuate arms 150, 152 adapted for encircling the glans 12 of the penis 10. A supporting arc portion 210 is coupled to the second end 132 and is contoured to conform to the pubic muscles 14 of the user of the device. The rod means 120 has an upward bend 122 with respect to the longitudinal axis of the device. Securement means 310 is coupled to the second end 132 for securing the device to the penis 10. The securement means 310 can be secured around the scrotum 16 as well as the penis 10 in order to secure the device properly.

Figure 2:
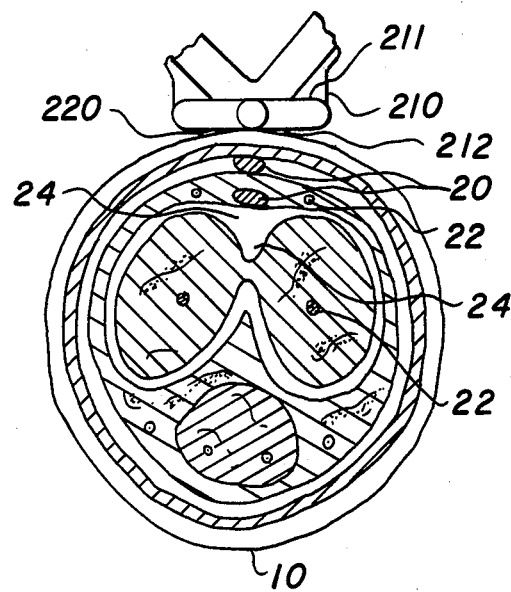
FIG. 2 is a sectional view of a penis showing an end section of the veinous vessels, the cavernosa, and arterial vessels.

FIG. 2 shows a cutaway view of the internal vessels of the penis in explaining how the instant invention improves performance of the external penile support device. In particular, there is shown a cross section of a penis 10 having portions including the veinous vessels 20, arterial vessels 22, and cavernosa portions 24 of the penis. There is also shown from an end view a cutaway portion view of the supporting arc portion 210 in use as it rests on the top of the root of the penis 10. In particular, the supporting arc portion 210 engages the root of the penis on the top thereof at contact surface area 220. In using the device, as a result of the weight of the penis and the constriction of the device around the root thereof by the securement means which is secured about the penis and scrotum area, pressure is applied to the penis which constricts the veinous vessels 20 of the penis. Penile erection is caused by engorgement of the penis with blood supply. As blood travels into the penis area by virtue of the arteries, yet is restricted from outflow by constriction of the vein vessels, then the blood supply is increased and constriction causes the erection to be initiated and remain for a longer period of time for satisfactory use and performance. As shown in FIG. 2, and in FIGS. 3 and 8, the bottom portion of the supporting arc 210 has a base portion 212. It is preferably, generally flat. This maximizes the amount of surface area which can comfortably engage the penis so as to constrict the veins and thereby enhance the erection of the penis. The wide base area is desirable in that a narrow area or rounded shape as shown in the prior art, while it may press down harder and deeper on the penis, may cause discomfort. Also, the prior art devices may not effectively constrict the veins if pressure is on an area where the vein is not located. In contrast, an improved feature of the present invention is that it utilizes a wider area to maximize the surface contact with vein locations on the penis, and it will more effectively constrict the flow of blood through the veins and conform to the penis shape due to the resiliency of the penis skin.

Moreover, the present invention, by utilizing such a base portion having greater surface area, still does not use a base so wide as to interfere with the use of the device when the penis enters the vagina of the user's partner during coitus. The shape and location of the base to realize the benefit of improved constriction blood flow, while not interfering with operation of the device, also has the added advantage of being more comfortable to the user thereof. By having the shape as disclosed herein, it is smoother and is less apt to be a protruding element which may cause pain and discomfort to the penis of the user of conventional prior art devices of this kind. This is especially true when the securement means 310 is secured about the penis and scrotum which can cause an increase of pressure at the point at which the supporting arc contacts and engages the penis.

Figure 9:
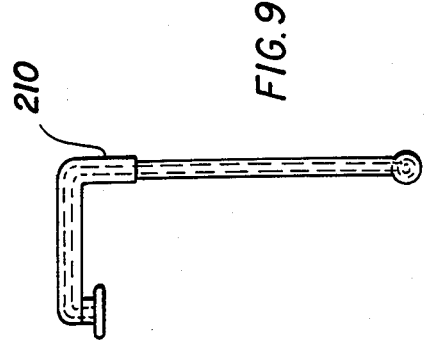
FIG. 9 is a side view of the embodiment shown in FIG. 7.
Figure 7:
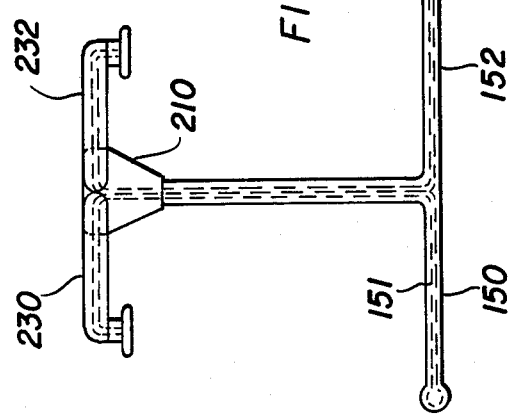
FIG. 7 is a top view of one embodiment in one step in the process of manufacturing a preferred embodiment of the present invention.
Figure 8:
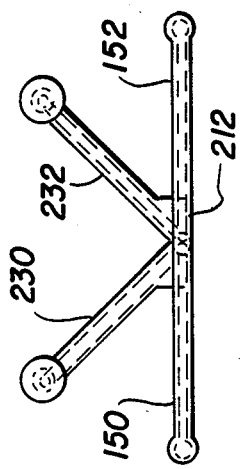
FIG. 8 is an end view of the embodiment shown in FIG. 7.

There is shown in FIGS. 3 through 5, and 7 through 9, steps in the process of forming the improved device herein. FIG. 7, 8, and 9 show top, end, and side views, respectively, of the improved device showing the arms 150, 152 prior to their having been formed to be in an arcuate shape. The supporting arc portion has arms 230, 232 which when first formed are in a straight shape so that the device can be custom fit as shown in FIG. 1 to contour to the pubic muscles 14 of the user. As in conventional devices, there are wire wrapped areas which are then covered with synthetic, flexible materila. Typically, it is a non-toxic elastic material such as rubber or latex, or similar material. Typically, there is formed a wire core filament wrapped about the rods as represented and shown in dotted lines in FIGS. 7, 8, and 9 as 151.

In particular, the present invention utilizes the supporting arc portion 210 which has supporting arms 230 and 232 as being a unitary integral construction, preferably ejection molded. This permits a one-piece construction not having crevices and the like which is typically found in the conventional prior art devices. This prevents accumulation of bacteria and other germs in crevices and the like since it is unitary structure and has no such crevices where an assembled part would have such places for harmful bacterial growth. In addition, its smooth form and appearance, since it is of unitary construction, and its decreased likelihood of being disassembled or falling apart, is an enhancement over the conventional prior art.

Figure 4:
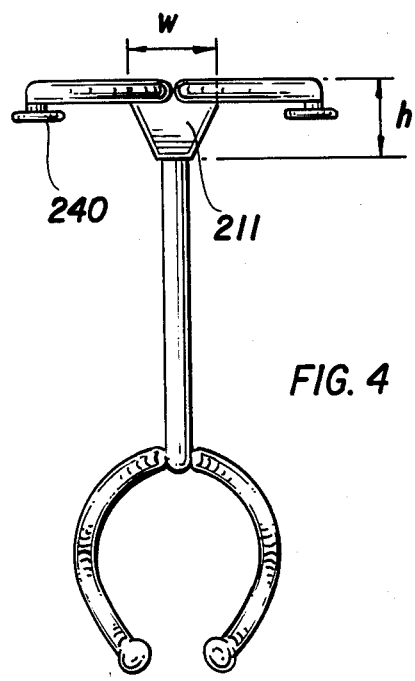
FIG. 4 is a diagrammatic top view of the embodiment shown in FIG. 3.

A preferred embodiment of the present invention incorporates the base supporting arc portion having a width of the triangular shaped base being approximately equal to the length of its height. The width is shown in FIG. 4 as width, and length as 1, in the top view in FIG. 4. While the base is shown as being preferably triangular shaped, any other such shape would suffice provided it does not interfere with the use of the device, yet realizes the benefit of applying pressure to the veins at the top of the root of the penis. The triangular shape is preferable in the sense that it is a gradual wedge shape with the point of the wedge pointing toward the head of the penis, which would correspond to the entry of the vagina in use of the device. In a preferred embodiment of the invention, the width w as shown in FIG. 4 of the base portion 211 of the supporting arc portion 210, is of a width w in relation to the inside diameter d of the arcuate arms 152, 150 shown in FIG. 3 of approximately a ratio of 3:4. In one preferred embodiment, there is a 14 millimeters width w of the base, and an internal diameter d of 18 millimeters. In a preferred embodiment of the invention, the width of the flat base is in the range of from 11 to 17 millimeters.

A distinct advantage of having the supporting arc means being formed integrally is that there are no open crevices in which bacteria can accumulate and cause infection and disease and the like. Also, it is readily adapted to sterilization processes if such is deemed appropriate in use of the device. In addition, since there are not a number of parts requiring assembly as in the prior art devices, there is less manufacturing cost, and the device is more suited to decreasing the expenses of maintaining and manufacturing the device.

Figure 5:
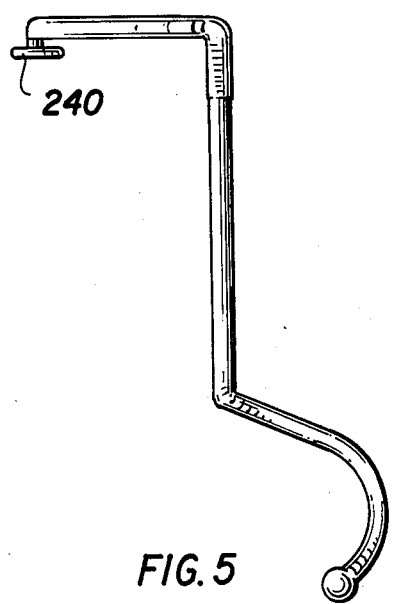
FIG. 5 is a side view of the embodiment shown in FIG. 3.
Figure 3:
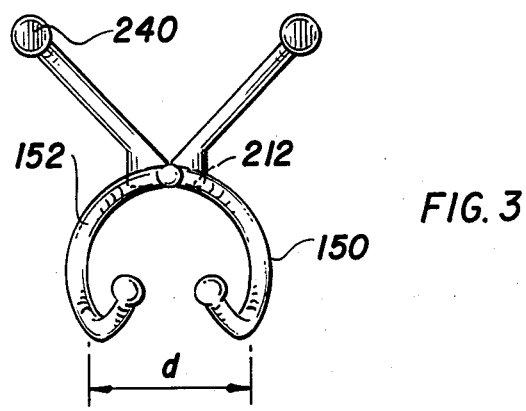
FIG. 3 is an end view of a preferred embodiment of the present invention.
Figure 6:
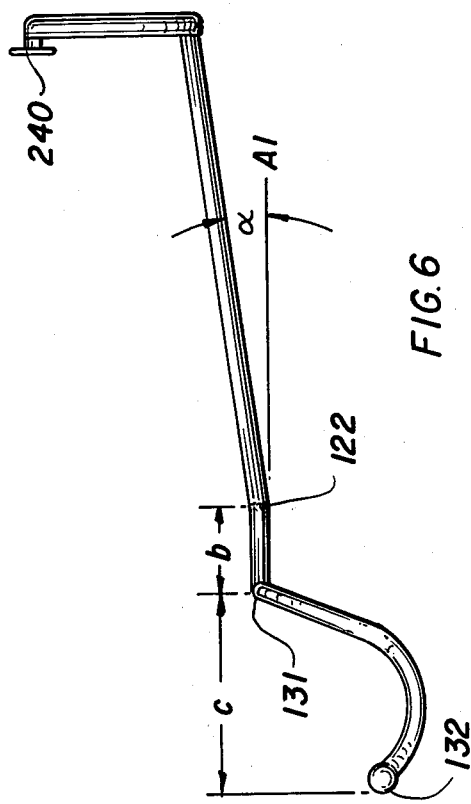
FIG. 6 is a side view of the preferred embodiment shown in FIG. 3 after a bend has been placed in the device.

In respect to FIGS. 3 through 5, after the device is formed, the bend 122 is placed in the device as shown in FIG. 6. The distance from the end 131 of the elongated rod 120 of the device to the bend at 122 is preferably approximately a distance of b as shown in FIG. 6. In a preferred embodiment, this distance b is approximately 25 to 40 percent of the distance c along the axis as shown in FIG. 6 from the tips of the arcuate arms which supports the glans to the end of the elongated rod at 131. In a preferred embodiment, the distance b is 13 millimeters, and the distance c is 35 millimeters. The purpose of this bend as known in the prior art is to enhance the constriction of the veins on the top of the penis. By the weight of the penis, and by its engorgement during erection, the bend point 122 enhances the operation of constricting vessels to stimulate and maintain an erection, in conjunction with the action of the improved supporting arc portion.

As further shown in FIG. 6, the downward bend is at some angle $\alpha$ to the axis A1. In the prior art embodiments, this angle was preferably indicated to be in the range of from 15 to 25 degrees. However, in the instant invention as disclosed herein, the amount of the bend is preferably of a lesser amount, typically in the range of from 5 to 15 degrees. In a preferred embodiment as disclosed herein, an angle of approximately 8 degrees is utilized to realize the benefits of the invention. The lesser bend is preferred in that it is not as discomforting. Moreover, because of the enhanced structure of the base portion in the present invention, an increased surface area 212 pressing against the root of the penis at supporting arc poriton 210 permits less pressure to be required at other contact portions along the top of the penis. Accordingly, less of an angle is required and is utilized in the present invention. Aside from increased comfort and less discomfort to the user thereof, there is the added advantage that the lesser bend is not as critical in terms of constricting veinous flow. In addition, in the conventional prior art devices, if the bend missed direct engagement with the appropriate vein in the top of the penis, it did not work as well as the instant device which more likely engages and causes constriction of the veins to enhance the maintenance of a erection.

Figure 10:
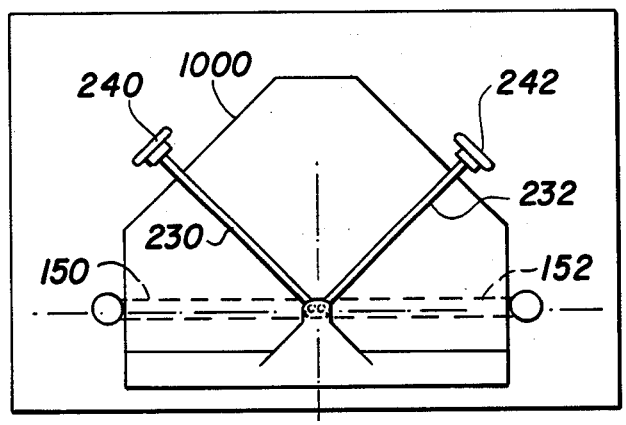
FIG. 10 is an end view of one portion of a process of manufacture of a preferred embodiment of the present invention.
Figure 11:
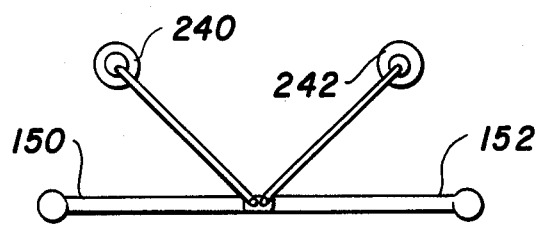
FIG. 11 is an end view of a step in the manufacturing process after bending of one portion of the device in the manufacture of same in accordance with the present invention.

Further improvements to the present invention over the prior art, are as shown in the construction thereof in FIGS. 10 and 11. In FIGS. 10 and 11 there is shown an end view of the device showing supporting arms 230, 232 being placed in a forming die 1000, and having arms 150 and 152 also placed therein prior to their being formed and shaped as shown in FIGS. 3 through 5, for example. The device in manufacturing operations is placed in the die, and the latched buttons 240, 242 are attached to the ends of the arms 230 and 232 respectively. In a preferred embodiment of the invention, the latch buttons are resistance welded in a perpendicular position to the end of the arms as shown in FIG. 10. Once they are in that position, then the device as it is being formed is placed in the forming die 1000, and the latch buttons are then bent at 90 degrees so the latch buttons are then in the position as shown in the end view of FIG. 11. The view in FIG. 11 is prior to the step in the manufacturing process and constructing of the device wherein the ejection molded supporting arm portion 210 is attached to the end of device as shown in FIG. 7. The advantages gained by using such a latch button over the previous and conventional prior art is that there is a solid attachment of the latch button to the supporting arms 240, 242 such that there are no open crevices which can have bacteria enter therein. Moreover, the positioning of the buttons at the 90 degree angle is conducive to attachment of the securement strap 310 as shown in FIG. 1 to the device as it is wrapped around the root of the penis and the scrotum area. In the prior art devices, the angle of the latch mechanism was not designed so as to function in the manner now presented. In addition, the ease of attaching the securement strap 310 is enhanced which has an important effect on operation of the device when it is being used by the impotent patient. The psychological factors of a device being easier to put on and take off for the user is an important element in using a device and being able to stimulate and maintain an erection.

Figure 12:
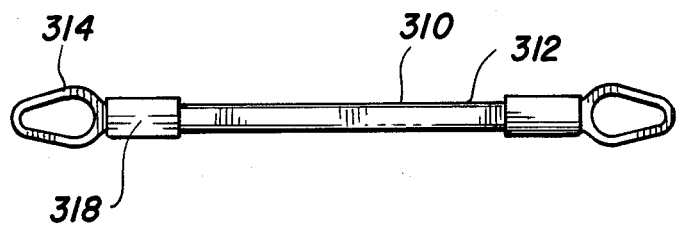
FIG. 12 is a diagrammatic top view of a preferred embodiment of a securement means in accordance with the present invention.
Figure 13:
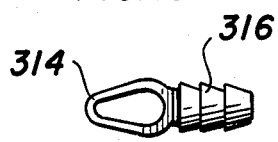
FIG. 13 is a diagrammatic top view of a portion of one embodiment of a latch loop mechanism which is part of the securement means shown in FIG. 12.

As shown in FIGS. 12 and 13, the securement strap 310 comprises tubing 312, preferably of an elastic kind, such as surgical tubing or the like, and a latch loop 314. The latch loop 314 has serrated edges 316 so that it can be pressed inside of a hollow and of the tubing 312 and then collar 318 can be pressed over it. The serrated edges then hold the tube between the collar and the edges for a secure fit. The tight fit also is an improvement over the prior art in that there are no open crevices which can permit bacteria to enter for infection and the like. In addition, the latch loop is flat so that it is easier to attach to the latch buttons 240, 242.

It is desirable that the material from which the device is made be the type of material used in surgical instruments, equipment, and devices. The surgical steel is preferable in terms of the metal parts, and surgical tubing and similar types of materials are preferable in the manufacture thereof. The latex rubber or other materials used for ejection molding, as well as other polymers, and suitable materials used should be sufficiently stiff to allow flexibility and comfort in use of the device. However, the under core which comprises the filament wrapped around the rods should be such that the portions which are to be bent will retain their shape once curved and fitted to the contours of the pubic muscle areas for example, of the securement means and primarily the supporting arc portion of the device.

Figure 14:
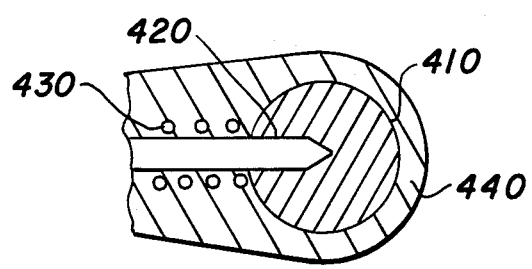
FIG. 14 is a sectional view of one end of the arcuate arms.

In another embodiment of the present invention, there is shown in FIG. 14 a section of one end of one of the arcuate arms 150, 152. It has an elongated rod core 420 wrapped with filament 430 and attached to sphere 410 by appropriate means, such as by resistance welding. This is assembled prior to being covered, via ejection molding or the like, with a covering material 440 such as rubber or latex. This offers an advantage of safety not found in the prior art devices, in that the sphere 410 would protect the user's partner during coitus from harm should the end of the rod break through the covering for some reason.

Another advantage of the present invention is that the device can be made of standardized sizes in accordance with the sizes encountered in the sizing of the devices by physicians and other medical specialists. By recognizing the benefits of the present invention and method and structure thereof, economies of scale in manufacturing can be realized, without inhibiting the effectiveness and use of the device in its intended purpose of maintaining an erection. Moreover, such a process lends itself to utilizing materials which can be quality controlled in conformance with various governmental regulations and requirements, as may be required in commercialization of the device.

In operation, it is intended that the device be fitted and contoured by a physician or medical specialist to the penis and pubic muscles of the user. Then the user is free to utilize the device in the privacy of his own home with the securement strap which works in an improved fashion over the conventional prior art methods.

Although the present invention has been shown and described in terms of specific preferred embodiments, it will be appreciated by those skilled in the art that changes or modifications are possible which do not depart from the inventive concepts described and taught herein. Such changes and modifications are deemed to fall within the purview of these inventive concepts. Thus, it should be noted that the accompanying description and drawings are meant to describe the preferred embodiments of the invention, but are not intended to limit the spirit and scope thereof.

What is claimed is:

1. An improved external penile support device for aiding penile erection of the type having an elongated rod means having first and second ends, a yoke coupled at the first end including arcuate arms adapted for and encircling the glans of the penis, a supporting arc portion at the second end being contoured to conform to the pubic muscles, the rod means having an upward bend with respect to the longitudinal axis, and securement means at the second end for securing the device to the penis, wherein the improvement comprises: said supporting arc portion further comprising means for applying pressure to the dorsal vein at the top of the root of the penis, said means for applying pressure having a generally flat base portion having a surface area for even applying of pressure to the veinous tissue of the penis for restricting flow of blood while maintaining comfort to the user thereof, the elongated rod means further comprising a core and filament wrapped thereon and a spherical portion attached to the end of the core prior to said end being covered with a covering material for improved safety and operation of the device.

2. The device of claim 1, wherein said spherical portion is attached to the end of the core of the rod by means of resistance welding.

* * * * *